(12) United States Patent
Shalev et al.

(10) Patent No.: US 11,918,804 B2
(45) Date of Patent: *Mar. 5, 2024

(54) METHOD AND DEVICE FOR SKIN TREATMENT BY HEATING AND MUSCLE STIMULATION

(71) Applicant: POLLOGEN LTD., Tel Aviv-Jaffa (IL)

(72) Inventors: Pinchas Shalev, Herzeliya (IL); Zion Azar, Shoham (IL)

(73) Assignee: POLLOGEN LTD., Tel Aviv (IL)

( * ) Notice: Subject to any disclaimer, the term of this patent is extended or adjusted under 35 U.S.C. 154(b) by 127 days.

This patent is subject to a terminal disclaimer.

(21) Appl. No.: 17/713,821

(22) Filed: Apr. 5, 2022

(65) Prior Publication Data

US 2022/0226645 A1 Jul. 21, 2022

Related U.S. Application Data

(63) Continuation of application No. 16/907,252, filed on Jun. 21, 2020, which is a continuation of application
(Continued)

(51) Int. Cl.
*A61H 9/00* (2006.01)
*A61B 18/04* (2006.01)
(Continued)

(52) U.S. Cl.
CPC .............. *A61N 1/322* (2013.01); *A61B 18/04* (2013.01); *A61H 9/0057* (2013.01); *A61H 23/00* (2013.01);
(Continued)

(58) Field of Classification Search
CPC .... A61N 1/322; A61N 1/328; A61N 1/36003; A61N 1/06; A61N 1/18; A61B 18/04;
(Continued)

(56) References Cited

U.S. PATENT DOCUMENTS 2,444,173 A 6/1948 Pierre
3,297,024 A 1/1967 Robinson
(Continued)

FOREIGN PATENT DOCUMENTS

CN 1721010 1/2006
EP 1568395 8/2005
(Continued)

OTHER PUBLICATIONS

Supplementary European Search Report—EP Application No. 10829624.5, dated Jan. 29, 2015.
(Continued)

*Primary Examiner* — Quang D Thanh
(74) *Attorney, Agent, or Firm* — ISUS INTELLECTUAL PROPERTY PLLC; Anthony Jason Mirabito

(57) ABSTRACT

A method and a system for treating skin tissue are provided. A heater is configured to modify temperature of the skin tissue, and a muscle stimulator is configured to provide muscle stimulation to a muscle layer located below the skin tissue. A handheld applicator is configured to be placed in vicinity of the skin tissue to deliver the temperature modification from the at least one heater to the skin tissue and the muscle stimulator from the muscle stimulator to the muscle layer located below the skin tissue; a control board is configured and operable to activate the at least one heater and the muscle stimulator according to respective activation pattern, thereby providing one or more treatments to the skin tissue.

18 Claims, 5 Drawing Sheets

Related U.S. Application Data

No. 15/587,487, filed on May 5, 2017, now abandoned, which is a continuation of application No. 13/510,062, filed as application No. PCT/IL2010/000947 on Nov. 16, 2010, now abandoned.

(60) Provisional application No. 61/261,381, filed on Nov. 16, 2009.

(51) Int. Cl.
  *A61H 23/00* (2006.01)
  *A61N 1/32* (2006.01)
  *A61N 1/36* (2006.01)
  *A61B 18/00* (2006.01)

(52) U.S. Cl.
  CPC ......... *A61N 1/328* (2013.01); *A61N 1/36003* (2013.01); *A61B 2018/00452* (2013.01); *A61H 2201/10* (2013.01); *A61H 2201/5007* (2013.01); *A61H 2207/00* (2013.01); *A61H 2230/50* (2013.01)

(58) Field of Classification Search
  CPC .......... A61B 2018/00452; A61B 18/12; A61H 9/0057; A61H 23/00; A61H 2201/10; A61H 2201/5007; A61H 2207/00; A61H 2230/50; A61H 23/02
  See application file for complete search history.

(56) References Cited

U.S. PATENT DOCUMENTS

| | | |
|---|---|---|
| 4,702,732 A | 10/1987 | Powers et al. |
| 5,169,398 A | 12/1992 | Glaros |
| 5,296,683 A | 3/1994 | Burkett et al. |
| 5,419,344 A | 5/1995 | DeWitt |
| 5,476,504 A | 12/1995 | Paolizzi |
| 5,562,706 A | 10/1996 | Lauterbach |
| 5,755,753 A | 5/1998 | Knowlton |
| 5,797,904 A | 8/1998 | Smith |
| 5,797,966 A | 8/1998 | Bontoux |
| 5,961,475 A | 10/1999 | Guity |
| 6,139,545 A | 10/2000 | Utely |
| 6,273,884 B1 | 8/2001 | Altshuler et al. |
| 6,277,116 B1 | 8/2001 | Utely |
| 6,425,912 B1 | 7/2002 | Knowlton |
| 6,546,934 B1 | 4/2003 | Ingle et al. |
| 6,692,490 B1 | 2/2004 | Edwards |
| 6,840,954 B2 | 1/2005 | Dietz et al. |
| 6,926,683 B1 | 8/2005 | Kochman et al. |
| 7,953,500 B2 | 5/2011 | Bingham et al. |
| 9,596,920 B2 | 3/2017 | Shalev et al. |
| 2001/0014815 A1 | 8/2001 | Matsumura et al. |
| 2002/0032441 A1* | 3/2002 | Ingle ................... A61N 1/403 606/41 |
| 2002/0120260 A1 | 8/2002 | Morris et al. |
| 2002/0165590 A1 | 11/2002 | Crowe |
| 2003/0032950 A1* | 2/2003 | Altshuler ............ A45D 44/005 606/9 |
| 2003/0187488 A1 | 10/2003 | Kreindel |
| 2004/0019350 A1 | 1/2004 | O'Brien |
| 2004/0073079 A1* | 4/2004 | Altshuler ............ A61B 18/203 600/1 |
| 2004/0220622 A1 | 11/2004 | Bernabei |
| 2005/0015085 A1 | 1/2005 | McClurken et al. |
| 2005/0107832 A1* | 5/2005 | Bernabei ................ A61N 1/327 607/3 |
| 2005/0154433 A1 | 7/2005 | Levy |
| 2005/0171583 A1 | 8/2005 | Mosher |
| 2005/0222565 A1 | 10/2005 | Manstein |
| 2006/0036300 A1 | 2/2006 | Kreindel |
| 2006/0205996 A1 | 9/2006 | Presthus |
| 2006/0206103 A1* | 9/2006 | Altshuler ............ A61B 18/203 606/9 |
| 2006/0206110 A1 | 9/2006 | Knowlton et al. |
| 2006/0217704 A1 | 9/2006 | Cockburn et al. |
| 2007/0055154 A1 | 3/2007 | Torbati |
| 2007/0055180 A1 | 3/2007 | Deem |
| 2007/0060989 A1 | 3/2007 | Deem |
| 2007/0123807 A1 | 5/2007 | Applebaum |
| 2007/0179490 A1 | 8/2007 | Azar |
| 2007/0198004 A1 | 8/2007 | Altshuler |
| 2007/0232966 A1 | 10/2007 | Applebaum et al. |
| 2008/0039914 A1 | 2/2008 | Cory |
| 2008/0103565 A1 | 5/2008 | Altshuler et al. |
| 2008/0195181 A1 | 8/2008 | Cole |
| 2008/0215039 A1* | 9/2008 | Slatkine ................ A61M 5/425 606/9 |
| 2008/0312646 A9 | 12/2008 | Peterson |
| 2008/0312648 A1 | 12/2008 | Peterson |
| 2009/0043293 A1 | 2/2009 | Pankratov |
| 2009/0156958 A1 | 6/2009 | Mehta et al. |
| 2009/0270963 A1 | 10/2009 | Pelger |
| 2010/0004715 A1 | 1/2010 | Fahey |
| 2010/0016850 A1 | 1/2010 | Ron Edoute |
| 2010/0042018 A1 | 2/2010 | Kleinsinger |
| 2010/0049186 A1 | 2/2010 | Ingle et al. |
| 2010/0057149 A1 | 3/2010 | Fahey |
| 2010/0174137 A1 | 7/2010 | Shim |
| 2010/0228304 A1 | 9/2010 | Kriksunov et al. |
| 2011/0009692 A1 | 1/2011 | Gross |
| 2011/0009737 A1 | 1/2011 | Manstein |
| 2011/0130618 A1 | 6/2011 | Ron Edoute |
| 2011/0224665 A1 | 9/2011 | Crosby et al. |
| 2011/0230931 A1 | 9/2011 | Hagege |
| 2012/0215141 A1 | 8/2012 | Peddicord |
| 2012/0027120 A1 | 10/2012 | Shalev et al. |
| 2012/0271206 A1 | 10/2012 | Shalev et al. |
| 2013/0018222 A1 | 1/2013 | Miroshnichenko |
| 2015/0164401 A1 | 6/2015 | Toth |
| 2015/0297908 A1 | 10/2015 | Alinsod |
| 2016/0121112 A1 | 5/2016 | Zion |
| 2016/0263387 A1 | 9/2016 | Alinsod |
| 2016/0346561 A1 | 12/2016 | Ron Edoute |
| 2016/0346568 A1 | 12/2016 | Rockweiler |
| 2017/0014395 A1 | 5/2017 | Shalev et al. |
| 2017/0143997 A1 | 5/2017 | Rockweiler |
| 2017/0023946 A1 | 8/2017 | Shalev et al. |
| 2021/0002336 A1 | 1/2021 | Shalev et al. |
| 2022/0018438 A1 | 6/2022 | Shalev et al. |
| 2022/0022664 A1 | 7/2022 | Shalev et al. |
| 2022/0226646 A1 | 7/2022 | Shalev et al. |
| 2022/0226647 A1 | 7/2022 | Shalev et al. |
| 2022/0226648 A1 | 7/2022 | Shalev et al. |
| 2022/0226649 A1 | 7/2022 | Shalev et al. |
| 2022/0233851 A1 | 7/2022 | Shalev et al. |
| 2022/0028078 A1 | 9/2022 | Shalev et al. |

FOREIGN PATENT DOCUMENTS

| | | |
|---|---|---|
| EP | 2476460 | 7/2012 |
| GB | 277882 | 9/1927 |
| JP | H119703 | 1/1999 |
| JP | 3041670 | 5/2000 |
| JP | 2001259047 | 9/2001 |
| JP | 2003010145 | 1/2003 |
| JP | 2003019215 | 1/2003 |
| JP | 2004522497 | 7/2004 |
| JP | 2007507317 | 3/2007 |
| JP | 2006520247 | 9/2007 |
| JP | 2008173231 | 7/2008 |
| JP | 2008537896 | 10/2008 |
| JP | 2008545462 | 12/2008 |
| JP | 2012065693 | 4/2012 |
| RU | 2153366 | 7/2000 |
| RU | 2005131621 | 2/2006 |
| WO | 0112089 | 2/2001 |
| WO | 2008058452 | 5/2008 |
| WO | 2009023568 | 2/2009 |

(56) References Cited

FOREIGN PATENT DOCUMENTS

WO         2012080394         6/2012
WO         2015014811         2/2015

OTHER PUBLICATIONS

Office Action—European Application No. 10829624.5, dated Feb. 20, 2015.
Office Action—Russian Application No. 2012123457, dated Sep. 19, 2014.
Office Action—Japanese Application No. 2012538469, dated Sep. 16, 2014.
Office Action—Chinese Application No. 201080051957.9, dated Jun. 4, 2014.
Office Action—Australian Application No. 2010317380, dated May 14, 2014.
Search Report—PCT Application No. PCT/IL2010/000947, dated Apr. 5, 2011.
Godfrey, Sheila, "10 Electricity" In: "Principles and Practice of Electricall Epilation", Oct. 16, 2001, Butterworth Heinemann, pp. 75-83.
Y.Y. Dribnokhod, Cosmetology, Rostov-on-Don, "Fenix", 2008, pp. 384-385.
Reply to office action filed Sep. 22, 2022—corresponding U.S. Appl. No. 17/678,484.
Reply to office action filed Oct. 26, 2022—corresponding U.S. Appl. No. 17/713,943.

\* cited by examiner

METHOD AND DEVICE FOR SKIN TREATMENT BY HEATING AND MUSCLE STIMULATION

RELATED APPLICATIONS

This application is a continuation of and claims priority to U.S. application Ser. No. 16/907,252, filed Jun. 21, 2020, which is a continuation of and claims priority to U.S. application Ser. No. 15/587,487, filed May 5, 2017, now abandoned, which is a continuation of and claims priority to U.S. application Ser. No. 13/510,062, filed May 16, 2012, now abandoned, which is a U.S. National Stage application from and claims priority to PCT Application No. PCT/IL2010/00947, filed Nov. 16, 2010, which claims priority from U.S. provisional application No. 61/261,381 filed on Nov. 16, 2009, all of which disclosures are herein incorporated by reference.

FIELD OF THE INVENTION

The present invention relates generally to a device and method for treating skin tissue by using a radio frequency (RF) generator combined with muscle stimulation (MS), including electrical muscle stimulation (EMS).

BACKGROUND OF THE INVENTION

Skin tissue comprises an outer epidermal layer overlaying a dermal layer. The dermal layer is in contact with a subcutaneous adipose layer referred to as fatty tissue. Massaging the skin is known to improve blood circulation in the subcutaneous adipose tissue and help release fat from the cells of the fatty tissue into the surrounding cellular matrix. The fat is then removed by the body's lymphatic system.

U.S. Pat. No. 5,961,475 to Guitay discloses a massaging device in which negative pressure is applied to the user's skin while massaging. The combined treatment increases the blood circulation in the subcutaneous adipose tissue and breaks connections between adipose cells in the tissue.

U.S. Pat. No. 6,273,884 to Altshuler et al. discloses simultaneous application of optical energy and negative pressure to the user's skin for treating skin defects.

There is however a need for improved methods to enhance the release of fat from adipose tissue to increase lymphatic drainage.

SUMMARY OF THE INVENTION

An aspect of an embodiment of the invention, relates to an apparatus and method for accelerating lymphatic drainage. The method includes applying RF energy to heat the adipose layer. Additionally the method includes massaging the skin above the area that is heated by RF energy. Further additionally the method includes electrical muscle stimulation (EMS) to contract the muscles below the heated area thus providing pressure on the adipose layer from below. The apparatus is designed to apply the above three methods either separately or any combination of them simultaneously: namely, massaging the skin from above, causing electrical muscle stimulation from below, and heating the fatty tissue with RF radiation.

In an exemplary embodiment of the invention, the RF energy is provided by a high frequency AC current, and the EMS energy is provided by a low current DC pulse signal. Optionally, the electrical energies (RF and EMS) are provided by a mono-polar configuration wherein the apparatus applied to the user's skin is provided with a first electrode of one polarity, and a second electrode of the opposite polarity is attached to the user or held by the user to form a closed circuit. Alternatively, the electrical energy may be provided by a bi-polar configuration wherein the apparatus applied to the user's skin includes two electrodes to form a closed circuit without attaching electrodes external to the apparatus to the body of the user. In some embodiments of the invention, the apparatus uses a multi-pole configuration wherein the apparatus includes multiple electrodes of both poles of the circuit.

In some embodiments of the invention, some electrodes provide RF energy and other electrodes provide EMS energy. Alternatively, the same electrodes are designed to synchronize the pulses and deliver any of the two currents by control of the apparatus.

In an exemplary embodiment of the invention, the skin massage may be performed by applying positive pressure, for example in the form of vibrations, pushing, pounding and the like. Alternatively or additionally, the skin massage may be performed by applying negative pressure, for example using a vacuum or suction and the like. Optionally, the element of the apparatus applying the pressure may be heated or cooled while applying the pressure.

In an exemplary embodiment of the invention, when the apparatus is placed m contact with the user ls skin an electric circuit is formed and electric current flows automatically from the electrode to the user. Optionally, the RF energy may be coordinated with the EMS energy so that both will be activated simultaneously or separately by control of the apparatus.

In an exemplary embodiment of the invention, the frequency of the RF energy is selected to heat the user's skin mainly at the adipose layer positioned under the apparatus. The EMS flow is designed to contract the muscles below the adipose layer causing pressure on the fatty cells from below.

In some embodiments of the invention, parameters related to the RF energy are user selectable, for example signal intensity, frequency, duration and the like, to optimize usage of the apparatus for different users or different positions on the body of the user. Optionally, the parameters related to the EMS energy can be modified to fit the needs of the user, for example by selecting intensity, frequency, duration and the like.

In some embodiments of the invention, parameters related to massaging the skin are user selectable, for example the vibration rate, duration of vibrations, intensity, temperature of the massaging element and the like. Alternatively, the massaging may be performed by manually pressing the apparatus on the user's skin and moving it over a designated area.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
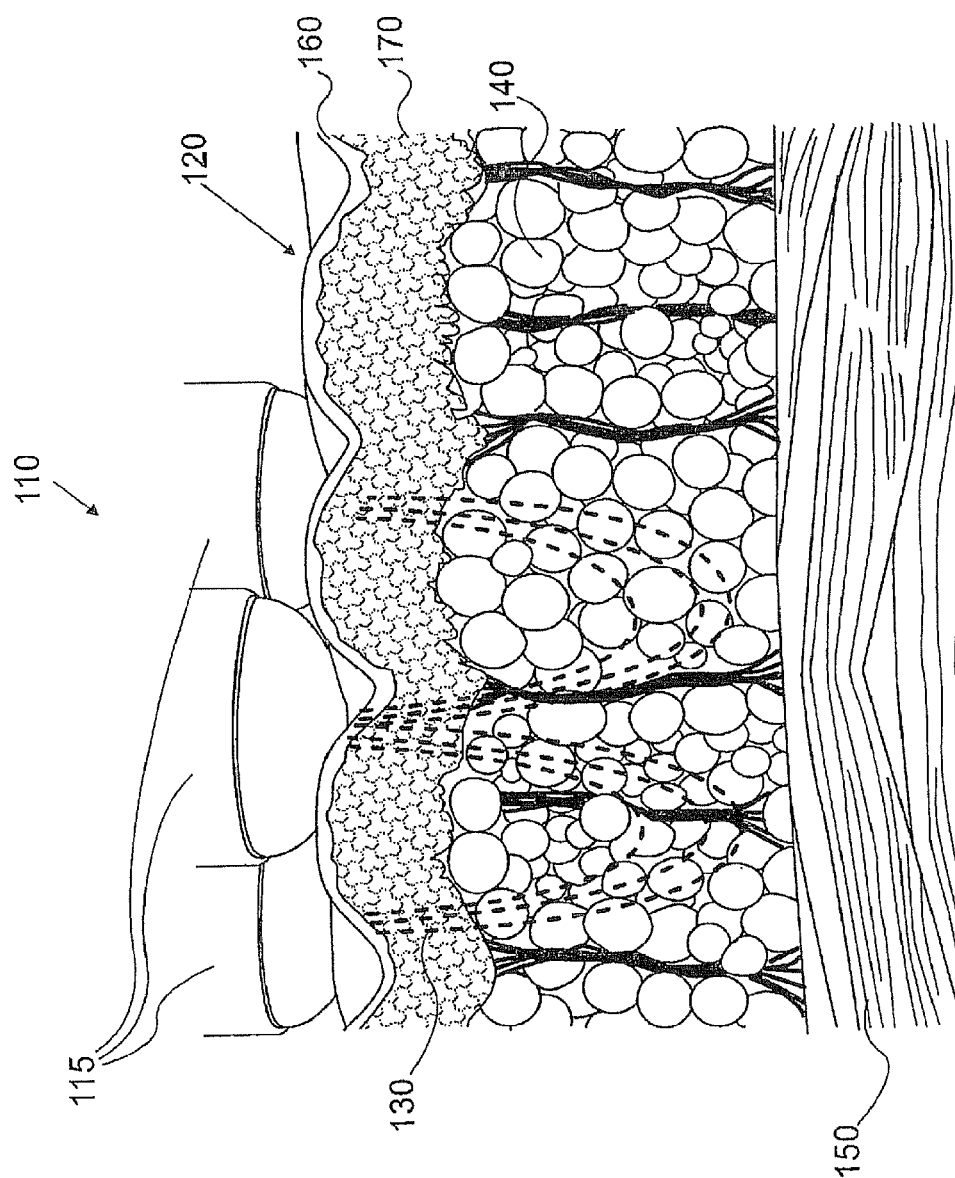
FIG. 1 is a schematic illustration of a fat reduction device deployed upon a user's skin, according to an exemplary embodiment of the invention.

FIG. 1 is a schematic illustration of a fat reduction device 110 deployed upon a user's skin 120, according to an exemplary embodiment of the invention. The skin 120 includes an upper epidermal layer 160, a lower dermal layer 170, and an adipose layer 140 (fat tissue layer). Muscles 150 are located below the adipose layer 140.

In an exemplary embodiment of the invention, fat reduction device 110 includes one or more heads 115 that serve as massage contacts and optionally also as electrodes for applying electrical energy. Optionally, fat reduction device 110 is adapted to perform at least three actions:

1. Massaging the outer layer of skin 120;
2. Heating the adipose layer 140 using RF energy 130 (e.g., with a frequency between 0.5 MHz to 2 MHz);
3. Stimulating the muscles 150 below the adipose layer 140 with an electrical muscle stimulation (EMS) signal (e.g., with pulses of DC current between +/−500 ma).

In an exemplary embodiment of the invention, fat reduction device 110 is deployed upon the user's skin 120 and applies pressure with heads 115 to massage the skin 120. Optionally the pressure may be in the form of vibrations, pushing, pounding, or other tactile forms. Alternatively, or additionally, the massaging may be in a negative form, for example by applying a vacuum or suction or similar form. FIG. 1 demonstrates how the skin 120 takes an uneven form due to the physical pressure exelied upon it. In some embodiments of the invention, fat reduction device 110 includes an element that applies the pressure, for example a motor a piezoelectric chip or other devices known in the art. Alternatively, the pressure may be exerted by manually pressing heads 115 against the user's skin.

In an exemplary embodiment of the invention, the RF energy 130 is delivered through the skin to the adipose layer 140. The RF energy 130 accelerates natural fat cell metabolism causing the release of liquefied fat from the cells into the extra cellular matrix. Additionally, the RF energy 130 heats collagen fibers and stimulates fibroblast metabolism resulting in tightening of the skin 120 and an increase in new collagen production.

Optionally, the physical pressure loosens the ties between the fat cells and together with the heating from the RF energy 130 accelerates release of liquefied fat from the fat cells. The heating and massaging also increase blood flow thus providing more nourishment to the area and removing dead cells and other impurities at all increased rate.

Figure 2:
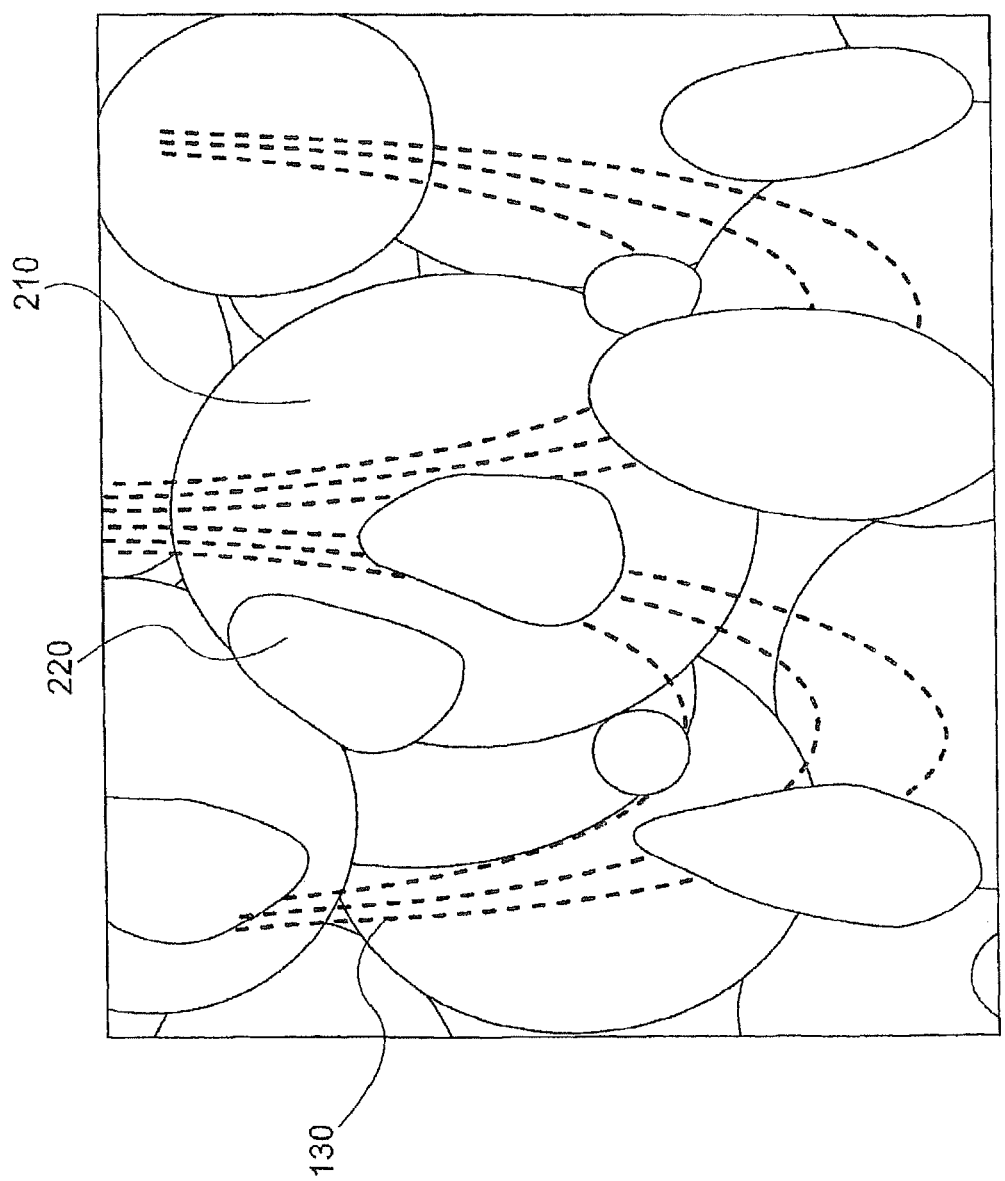
FIG. 2 is a schematic illustration of liquefied fat exiting from fat cells into the extra cellular matrix responsive to the use of the fat reduction device, according to an exemplary embodiment of the invention.

FIG. 2 is a schematic illustration of liquefied fat 220 exiting from fat cells 210 into the extra cellular matrix responsive to the use of the fat reduction device 110, according to an exemplary embodiment of the invention. In an exemplary embodiment of the invention, the RF energy is set to heat the fat cells 210 to a level wherein the temperature on the surface of the skin does not exceed 40° C.-45° C. to prevent skin damage. Optionally, higher temperature ranges may be possible for short durations.

Figure 3:
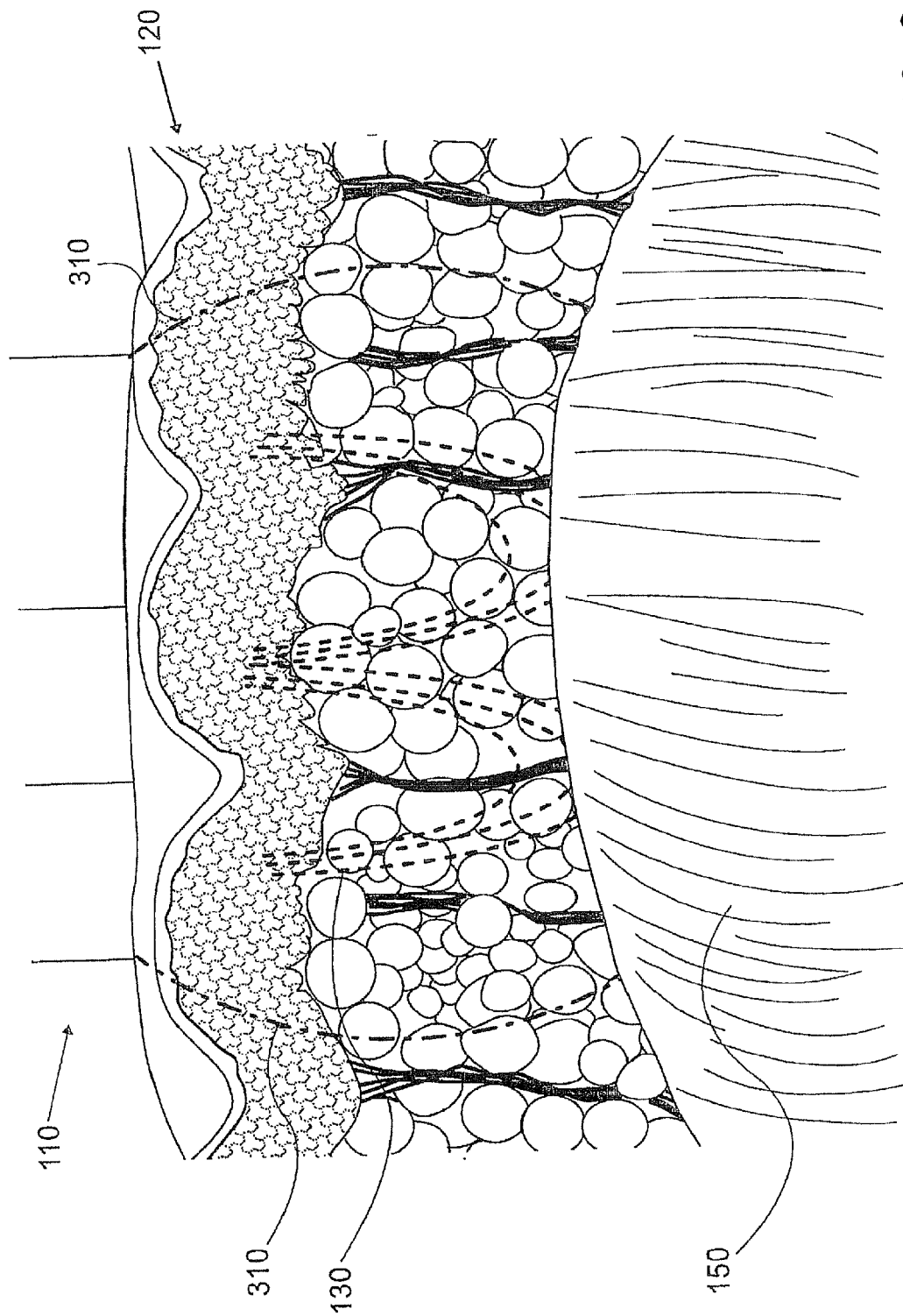
FIG. 3 is a schematic illustration of a fat reduction device applying an electrical current to stimulate a user's muscles, according to an exemplary embodiment of the invention.

FIG. 3 is a schematic illustration of fat reduction device 110 applying an electrical current 310 to stimulate the user's muscles 150, according to an exemplary embodiment of the invention. In an exemplary embodiment of the invention, electrical current 310 from the electrical muscle stimulation (EMS) pulse causes the muscles 150 to contract below the adipose layer 140, which causes a dual force to be applied to the fat cells 210. From above the adipose layer 140 is pressured physically by fat reduction device 110 and from below the EMS signals cause the muscles 150 to exert pressure on adipose layer 140. In some embodiments of the invention, the RF energy 130 and/or the EMS pulse may be activated by an activation switch on fat reduction device 110. Alternatively, they may be activated upon contact with the user's skin, for example by closing a circuit through the user's skin or by applying pressure on the head of fat reduction device 110.

Figure 4:
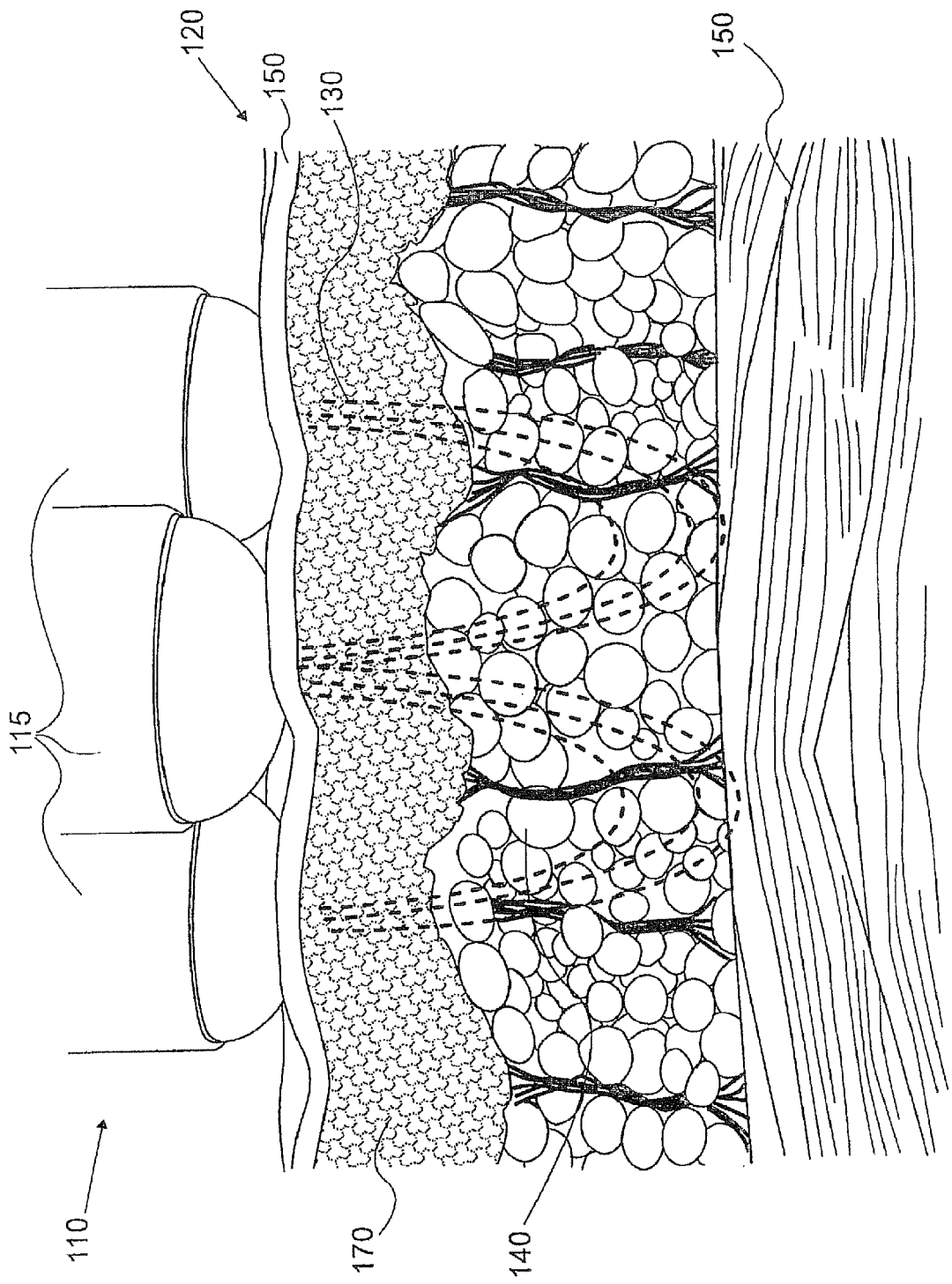
FIG. 4 is a schematic illustration of a fat reduction device and the user's skin following use of the fat reduction device, according to an exemplary embodiment of the invention.

FIG. 4 is a schematic illustration of fat reduction device 110 and the user's skin 120 following use of fat reduction device 110, according to an exemplary embodiment of the invention. Optionally, after applying fat reduction device 110 the distance between the muscles 150 and the epidermal layer 160 is reduced due to the exit of liquefied fat from the fat cells 210 of the adipose layer 140. Additionally, the epidermal layer 160 becomes smoother due to the tightening resulting from the collagen production as described above.

Figure 5:
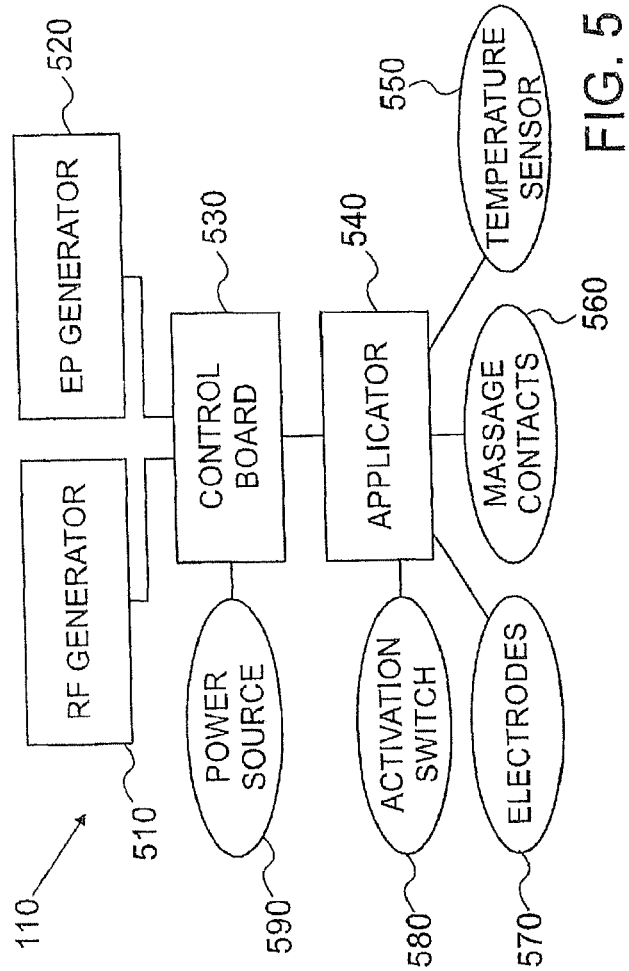
FIG. 5 is a schematic block diagram of the elements of a fat reduction device, according to an exemplary embodiment of the invention.

FIG. 5 is a schematic block diagram of the elements of fat reduction device 110, according to an exemplary embodiment of the invention. In an exemplary embodiment of the invention, fat reduction device 110 includes an RF generator 510 to provide an AC current in the form of a radio frequency (RF) electrical pulse for heating the user's skin 120. Optionally the AC signal is a low current signal, for example of about 1-10 ma, 24 VAC with a frequency between 0.5 MHz-2 MHz to prevent damage to the user's skin 120. In an exemplary embodiment of the invention, fat reduction device 110 also includes an electric pulse (EP) generator 520 that provides low current DC pulse signals, for example between +500 ma to −500 ma to cause the muscles 150 to expand and contract. In an exemplary embodiment of the invention, fat reduction device 110 includes a control board 530 that determines the actions of the device. Optionally, control board 530 may be a general purpose computer or a dedicated circuit. Control board 530 controls the duration, intensity, frequency and any other parameters of the electric pulses of the electrical current 310 for stimulating the muscles 150, and the RF energy 130 for heating the adipose layer 140. Additionally, the control board 530 determines the timing for applying the EP signal and the RF signal. In some embodiments of the invention, control board 530 includes a CPU, a memory, and input/output devices, for example a keypad and a screen.

In some embodiments of the invention, the control board accepts measurements from various sensors and controls fat reduction device 110 responsive to the measurements, for example temperature readings from a temperature sensor 550, which may include a thermistor or thermocouple monitoring the skin temperature. Optionally, the sensors may be placed in head 115, for example adjacent to the electrodes.

In a 11 exemplary embodiment of the invention, fat reduction device 110 includes an applicator 540 for applying the actions described above. In an exemplary embodiment of the invention, fat reduction device 110 is fed from a power source 590. Optionally, the power source 590 may be an internal power source, for example a battery. Alternatively, power source 590 may be an external power source, for example by connecting a power cable to a standard household power outlet.

In an exemplary embodiment of the invention, applicator 540 includes one or more heads 115 that serve as massage contacts 560, and electrodes 570. In some embodiments of the invention, the applicator may include an activation switch 580 to turn on and off fat reduction device 110, Optionally, activation switch 580 may be independently controlled by the user or may be automatically controlled, for example by placing fat reduction device 110 in contact with the user's body so that an electric circuit is formed or by pressing the fat reduction device 110 against the user's body causing the activation switch 580 to be depressed.

In some embodiments of the invention, fat reduction device 110 may use a mono-polar configuration wherein one pole of the circuit is represented by one or more electrodes on heads 115 and placed in contact with the user's skin. Optionally, the opposite pole is placed as a patch on the user's body or on a handle for grasping fat reduction device 110, to form a closed circuit. Alternatively, fat reduction device 110 may use a bi-polar configuration wherein both poles are represented by electrodes on the head 115 of the device, and no external electrodes are required. In some embodiments of the invention, a multi-polar configuration is used, with multiple electrodes wherein some of the electrodes on head 115 represent a first pole of the circuit and some represent the opposite pole. Optionally, the polarity of the electrodes may be controlled by control board 530, and their polarity may alternate during use of fat reduction device 110.

In some embodiments of the invention, some of the electrodes deliver RF energy 130 and some deliver electrical current 310. Alternatively, the same electrodes may deliver RF energy 130 and electrical current 310 intermittently. In some embodiments of the invention, electrical current 310 from the electrical muscle stimulation (EMS) signal is applied independent of the RF energy signal 130.

In an exemplary embodiment of the invention, control 530 controls the actions of the massage contacts 560. Optionally, the massage contacts 560 may include a motor, a piezoelectric element, a suction, a vacuum or other devices to massage the user's skin either positively or negatively. In an exemplary embodiment of the invention, the action of massage contacts 560 are synchronized with the electrical muscle stimulation (EMS) so that the adipose layer will be pressurized on both sides simultaneously. Alternatively, each function may act independently. In some embodiments of the invention, the massage is applied manually by pressing massage contacts 560 against the user's skin 120, and optionally moving them back and forth across the user's skin 120. Optionally, massage contacts 560 may be made from a soft material or hard material selected for providing a comfortable feeling to the user while massaging the user's skin 120. In some embodiments of the invention, the massage contacts 560 may include a heater to warm the contacts to enhance comfort and/or effectiveness of the massage.

Figure 6:
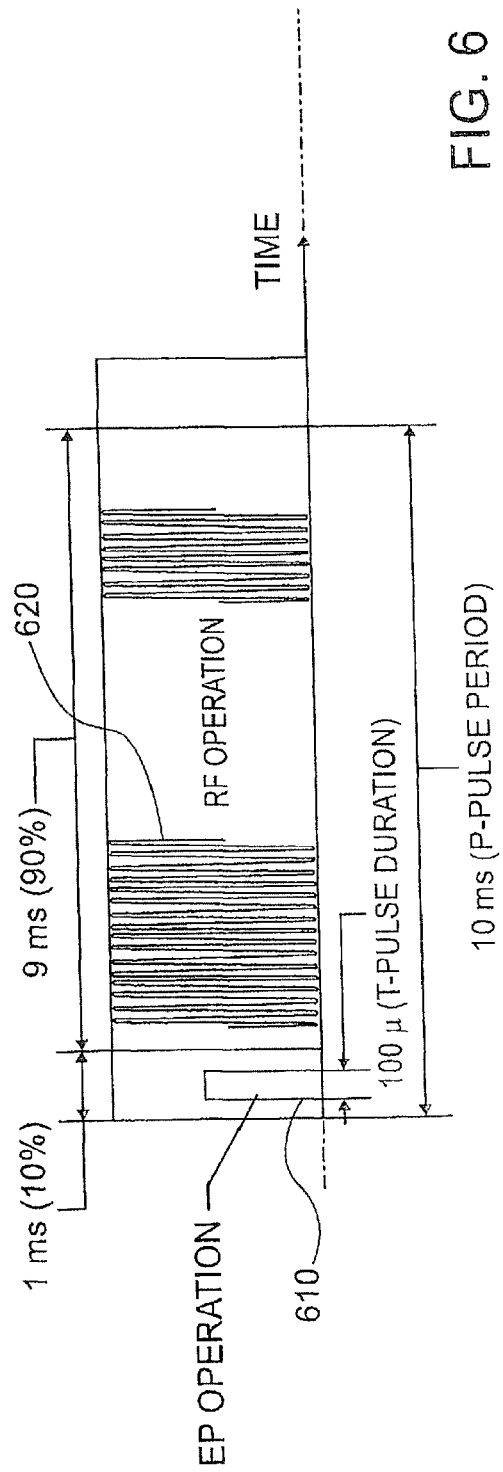
FIG. 6 is a schematic illustration of an RF signal combined with an EMS signal, according to an exemplary embodiment of the invention.

FIG. 6 is a schematic illustration of an RF energy signal synchronized with an EMS signal, according to an exemplary embodiment of the invention. In an exemplary embodiment of the invention, an electric pulse 610 of for example 100 micro-seconds is provide during an interval of 1 ms after which a RF• energy signal 620 is applied, for example for a duration of 9 ms. This sequence is applied repetitively while the fat reduction device is activated. Optionally, other duration may be used, for example the duration of electric pulse 610 may be longer than the duration of RF radiation signal 620 or vice versa.

It should be appreciated that the above-described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

The invention claimed is:

1. A method of treating a person's skin tissue, comprising:
providing a skin tissue treatment apparatus comprising:
at least one heater configured to cause temperature modification of a surface of the skin tissue,
a muscle stimulator configured to provide muscle stimulation to a muscle layer located below the skin tissue, and
a handheld applicator configured to be placed in vicinity of the surface of the skin tissue to deliver said temperature modification from said at least one heater to the surface of the skin tissue and said muscle stimulation from said muscle stimulator to the muscle layer located below the skin tissue;
providing a control board configured and operable to activate the at least one heater to heat the skin tissue surface to a temperature above 40 degrees C. and less than 45 degrees C. and the muscle stimulator according to respective activation patterns, wherein the control board is not configured to control cooling through the handheld applicator; and
placing the handheld applicator in the vicinity of the skin surface and operating the control board to deliver heat from said heater through the skin surface and muscle stimulation from the muscle stimulator to the muscle layer below the skin surface, wherein the operating of the control board does not deliver cooling through the handheld applicator to the surface of the skin tissue;
thereby providing one or more treatments to the skin tissue.

2. The method according to claim 1, wherein said respective activation patterns provide at least one of the following skin tissue treatments: skin tightening, fibroblast metabolism, collagen production and reducing distance between epidermis and the muscle layer.

3. The method according to claim 1, wherein said handheld applicator comprises one or more heads configured to contact the skin tissue during said one or more treatments, the one or more heads comprise one or more electrodes in electrical communication with said at least one heater and/or said muscle stimulator.

4. The method according to claim 3, wherein at least one electrode of the one or more electrodes is in electrical communication with said at least one heater and said muscle stimulator.

5. The method according to claim 3, wherein said one or more electrodes comprise one or more monopolar electrodes, and wherein respective one or more return electrodes are located outside the handheld applicator.

6. The method according to claim 3, wherein said one or more electrodes comprise one or more multipolar electrode arrangements comprising at least one of the following:
bi-polar electrodes;
at least three electrodes, with at least one electrode representing a first pole of a circuit
and at least two electrodes representing an opposite pole of the circuit.

7. The method according to claim 1, wherein said activation patterns of said at least one heater and the muscle stimulator are user selectable and include one or more of the following: signal intensity, frequency, and duration, thereby enabling to optimize the one or more treatments for different users or different positions on a person's skin tissue surface.

8. The method according to claim 1, wherein said control board is configured and operable to activate said at least one heater and the muscle stimulator in one or more of the following activation patterns: sequentially, intermittently and simultaneously.

9. A system for treating a person's skin tissue, comprising:
a skin tissue treatment apparatus comprising:
at least one heater configured to cause temperature modification of a surface of the skin tissue,
a muscle stimulator configured to provide muscle stimulation to a muscle layer located below the skin tissue,
a handheld applicator configured to be placed in vicinity of the skin tissue to deliver said temperature modification from said at least one heater to the surface of the skin tissue and muscle stimulation from said muscle stimulator to the muscle layer located below the skin tissue;
and
a control board configured with a heater activation pattern and a muscle stimulator activation pattern, and without any cooling activation pattern, and operable to activate the at least one heater to heat the skin tissue surface to a temperature above 40 degrees C. and less than 45 degrees C. and the muscle stimulator according to the respective activation patterns; wherein the control board is configured to operate the heater and the muscle stimulator according to the respective heating and muscle stimulator activation patterns thereby providing one or more treatments to the skin tissue.

10. The system according to claim 9, wherein said respective activation patterns provide at least one of the following skin tissue treatments: skin tightening, fibroblast metabolism, collagen production and reducing distance between epidermis and the muscle layer.

11. The system according to claim 9, wherein said handheld applicator comprises one or more heads configured to contact the skin tissue during said one or more treatments, the one or more heads comprise one or more electrodes in electrical communication with said at least one heater and/or said muscle stimulator.

12. The system according to claim 11, wherein at least one electrode of the one or more electrodes is in electrical communication with said at least one heater and said muscle stimulator.

13. The system according to claim 11, wherein said one or more electrodes comprise one or more monopolar electrodes, and wherein respective one or more return electrodes are located outside the handheld applicator.

14. The system according to claim 11, wherein said one or more electrodes comprise one or more multipolar electrode arrangements comprising at least one of the following:
bi-polar electrodes;
at least three electrodes, with at least one electrode representing a first pole of a circuit and at least two electrodes representing an opposite pole of the circuit.

15. The system according to claim 11, wherein said muscle stimulator comprises an electrical pulse generator configured to provide electrical muscle stimulation signal (EMS) to the muscles in the muscle layer located below the skin tissue, and wherein said one or more electrodes are configured to deliver the electrical muscle stimulation signal to the skin tissue.

16. The system according to claim 9, wherein said handheld applicator comprises one or more sensors configured to provide measurements indicative of the one or more treatments to the control board, the control board being thereby configured to determine parameters of the activation patterns based on the one or more sensors measurements.

17. The system according to claim 9, wherein said control board is configured and operable to activate said at least one heater and said muscle stimulator in one or more of the following activation patterns:
sequentially, intermittently and simultaneously.

18. A system for treating a person's skin tissue, consisting essentially of:
a skin tissue treatment apparatus, wherein the skin treatment apparatus includes:
at least one heater configured to cause temperature modification of a surface of the skin tissue,
a muscle stimulator configured to provide muscle stimulation to a muscle layer located below the skin tissue,
a handheld applicator configured to be placed in vicinity of the skin tissue to deliver the temperature modification from the at least one heater to the skin tissue and the muscle stimulation from the muscle stimulator to the muscle layer located below the skin tissue;
and
a control board configured with a heater activation pattern and a muscle stimulator activation pattern, and operable to activate the at least one heater to heat the skin tissue surface to a temperature above 40 degrees C. and less than 45 degrees C. and the muscle stimulator according to the respective activation patterns; wherein the control board is configured to operate the heater and the muscle stimulator according to the respective activation patterns thereby providing one or more treatments to the skin tissue.

* * * * *